United States Patent [19]
Webster, Jr.

[11] Patent Number: 5,431,168
[45] Date of Patent: Jul. 11, 1995

[54] STEERABLE OPEN-LUMEN CATHETER

[75] Inventor: Wilton W. Webster, Jr., Altadena, Calif.

[73] Assignee: Cordis-Webster, Inc., Baldwin Park, Calif.

[21] Appl. No.: 112,241

[22] Filed: Aug. 23, 1993

[51] Int. Cl.⁶ .............................. A61B 5/00
[52] U.S. Cl. ........................ 128/658; 604/95; 604/280
[58] Field of Search ............ 128/657, 658, 772; 604/95, 280-283

[56] References Cited

U.S. PATENT DOCUMENTS

| | | | |
|---|---|---|---|
| 4,586,923 | 5/1986 | Gould et al. | 128/657 |
| 4,723,936 | 2/1988 | Buchbinder et al. | 128/657 |
| 4,798,598 | 1/1989 | Bonello et al. | 128/658 |
| 4,920,980 | 5/1990 | Jackowski | 128/658 |
| 5,277,199 | 1/1994 | DuBois et al. | 128/657 |

FOREIGN PATENT DOCUMENTS 2019151  11/1992  WIPO .................. 128/772

Primary Examiner—Max Hindenburg
Attorney, Agent, or Firm—Christie, Parker & Hale

[57] ABSTRACT

A steerable catheter comprises an elongated catheter body and a tip portion. First and second lumens extend through the catheter body and tip portion. The first lumen is open at the distal end of the catheter. The second lumen is off-axis. A tightly wound coil spring is disposed in the second lumen and extends the length of the catheter body. The coil spring is fixed at the ends of the catheter body. A puller wire is slidably disposed within the coil spring, its distal end extending into and fixed at the distal end of the tip portion. The proximal end of the puller wire is attached to a control handle. Manipulation of the control handle results in deflection of the tip portion without deflection of the catheter body.

18 Claims, 5 Drawing Sheets

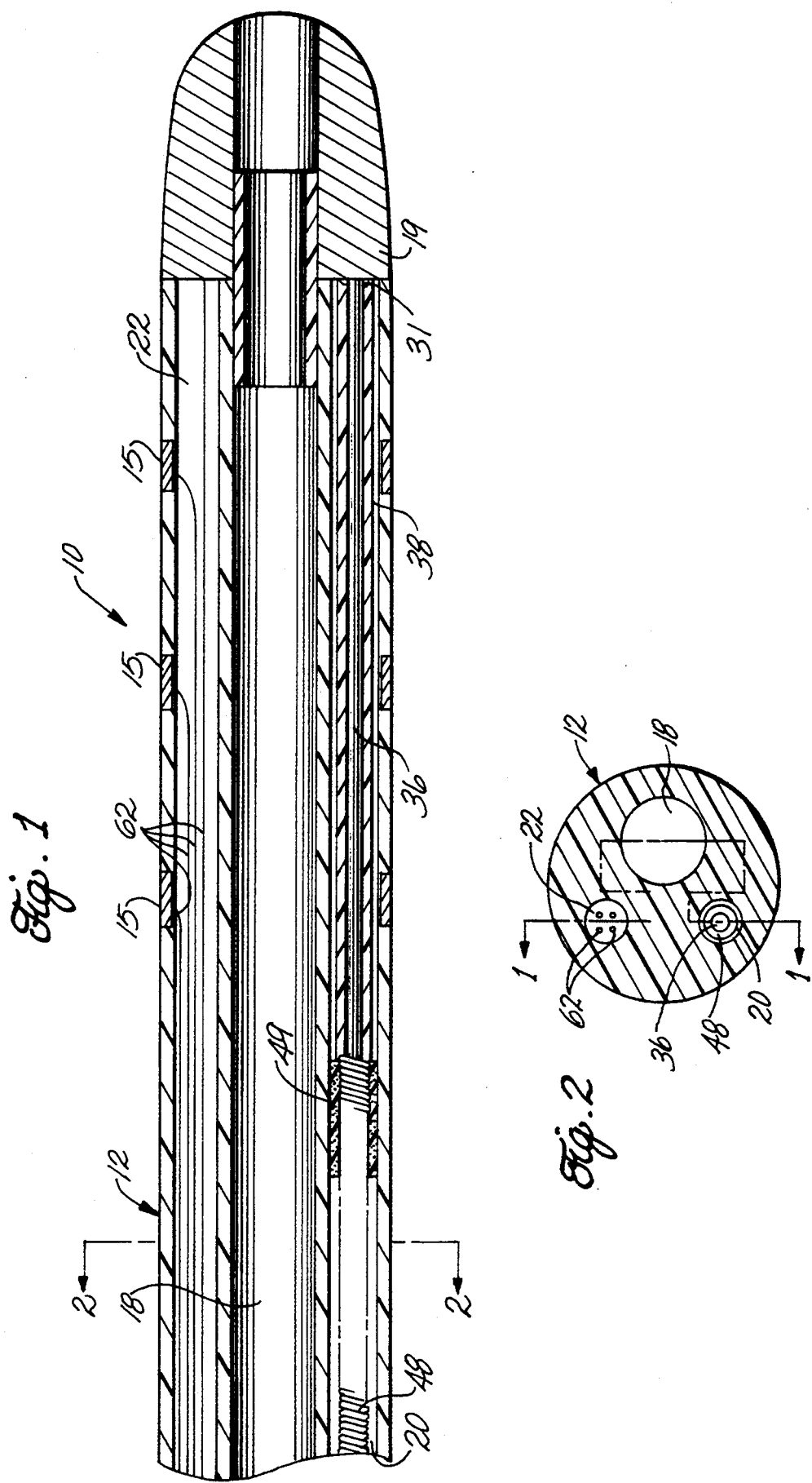

STEERABLE OPEN-LUMEN CATHETER

FIELD OF THE INVENTION

This invention relates to steerable catheters for use in a body lumen, and more specifically to an electrode catheter having a steerable tip and an open lumen.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable tip electrode catheters are now well known. Such a catheter generally has a control handle at its proximal end for controlling deflection of the tip in one or more directions. For example, U.S. Pat. No. 4,960,134 to applicant discloses a particularly useful steerable tip catheter. This catheter comprises a puller wire which extends on-axis through an elongated reinforced catheter body and then off-axis in a deflectable tip portion. In this arrangement, longitudinal movement of the puller wire relative to the catheter body results in deflection of the catheter tip portion. The catheter body tends not to deflect for two reasons. First, it is reinforced and therefore resists compression. Second, the puller wire extends coaxially within the catheter body. The compressive forces on the catheter body are generally uniformly distributed across the catheter body and deflection is thereby minimized. This allows precise rotational control of the catheter body and tip.

In certain applications, it is desirable to have the ability to inject and/or withdraw fluid through the catheter. This is accomplished by means of an open lumen catheter. For example, it is known that in cardiac ablation procedures using radiofrequency (RF) energy, there is a tendency for the ablation electrode to overheat. If overheating occurs, a coagulum forms on the surface of the electrode and the catheter must be withdrawn, cleaned and reinserted for proper use.

It is known that the ablation electrode can be cooled by the passage of a cooling fluid, e.g., saline solution, through a lumen in the electrode. In a small diameter ablation catheter, e.g., 8 French or less, the size of a lumen sufficient to pass a cooling fluid through the catheter to cool the ablation electrode is such that it does not permit the presence of an on-axis puller wire. That is, the puller wire must extend through the catheter off-axis. In such a catheter, longitudinal movement of the puller wire relative to the catheter body results in not only deflection of the tip, but of the catheter body itself. This makes rotation of the catheter, particularly if the catheter is curved around a vascular bend, exceedingly difficult to control. Thus, conventional designs for small diameter catheters with deflectible tips cannot provide for an open lumen without loss of tip control.

SUMMARY OF THE INVENTION

This invention provides a steerable open-lumen catheter with improved tip control. The catheter comprises an elongated catheter body, a tip portion at the distal end of the catheter body and a control handle at the proximal end of the catheter body. At least two lumens extend through the catheter body and tip portion.

The first lumen has a diameter of at least about one-third and preferably at least about one-half the outer diameter of the catheter body. For small diameter catheters having an outer diameter of less than 0.1 inch, the diameter of the first lumen is at least about 0.03 inch and preferably at least about 0.05 inch. The first lumen is open at the distal end of the tip portion. The first lumen provides a pathway for the passage of fluids through the catheter, or movement of a mechanical element, such as an optic fiber, anchoring wire or the like, through the catheter.

The second lumen is off-axis and comprises an elongated, flexible, but non-compressible tightly wound coil spring fixedly disposed within the portion of the second lumen extending through the catheter body. A puller wire is slidably mounted within and extends through the coil spring into the tip portion. The distal end of the puller wire is fixedly attached to the tip portion at or adjacent to the distal end of the tip portion. The proximal end of the puller wire is attached to the control handle for moving the puller wire longitudinally relative to the catheter body and coil spring. By this arrangement, longitudinal movement of the puller wire relative to the catheter body and coil spring results in deflection of the catheter tip with minimal and preferably no deflection of the catheter body.

Preferably, a flexible, compressible, lubricous sleeve surrounds the puller wire in the tip portion. A sleeve made of polytetrafluoroethylene is presently preferred. In a particularly preferred embodiment of the invention, the tip portion carries one or more electrodes, including a tip electrode. In such an embodiment, the first lumen extends through the tip electrode and the distal end of the puller wire may be attached directly to the tip electrode. There is preferably provided a third lumen which extends through the catheter body and tip portion and provides a passageway for electrode lead wires. The electrode lead wires extend from the electrodes carried on the tip portion through the catheter body and control handle to one or more plugs which are electrically connected to an electrical stimulator and/or recorder, an RF energy source or the like.

BRIEF DESCRIPTION OF THE DRAWINGS

These and other features and advantages of the present invention will be better understood by reference to the following detailed description when considered in conjunction with the accompanying drawings wherein:

FIG. 1 is a longitudinal offset cross-sectional view of a preferred three lumen electrode catheter constructed in accordance with the present invention, showing all three lumens;

FIG. 2 is a transverse cross-sectional view of the catheter body of FIG. 1 along line 2—2.

DETAILED DESCRIPTION

Figure 3:
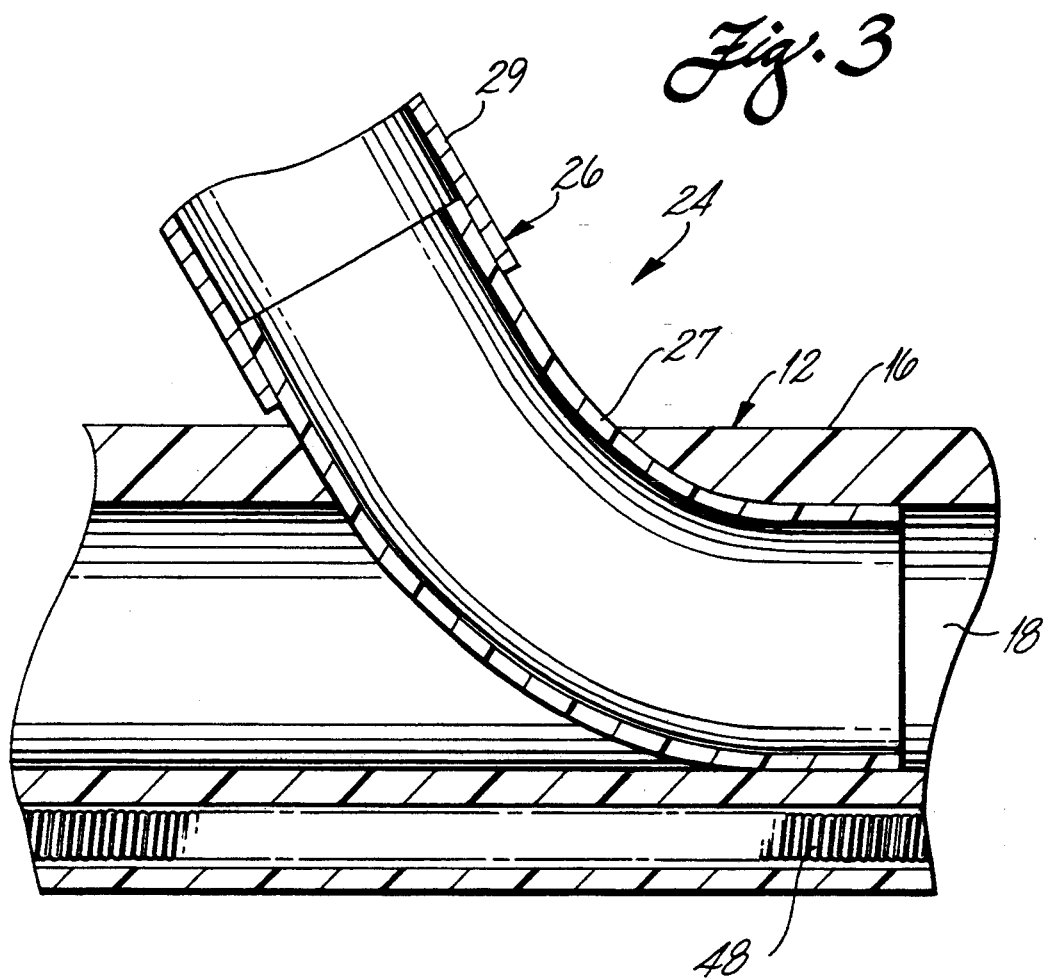
FIG. 3 is a longitudinal cross-sectional view of the proximal end of a preferred catheter showing a fitting for the injection or withdrawal of fluid through the open lumen of the catheter body.

FIGS. 1, 2 and 3 illustrate a particularly preferred cardiovascular electrode ablation catheter constructed in accordance with the present invention. The catheter comprises an elongated catheter body 12 having proximal and distal ends. A catheter tip portion 14 extends from the distal end of the catheter body 12 and a control handle (not shown) is provided at the proximal end of the catheter body. With reference to FIG. 2, the catheter 10, including the catheter body 12 and tip portion 14 comprises first, second and third lumens 18, 20 and 22 respectively.

The length and diameter of the catheter body 12 are not critical and may vary according to the application. For the cardiovascular catheter shown in the accompanying drawing, a length of about 40 to 48 inches and an outer diameter of about 0.1 inch (7 or 8 French) is preferred.

The catheter tip portion 14 preferably has a short length of about 2 to 3 inches. The diameter is preferably about the same as that of the catheter body 12 or may be slightly less (e.g., 6½-7 French) than the diameter of the catheter body 12.

The catheter tip portion 14 carries a plurality of electrodes, including ring electrodes 15 and a tip ablation electrode 19. It is understood that the number, size, and spacing of the electrodes may vary as desired. In the embodiment shown, tip electrode 19 is mounted at the distal end of the tip portion 14 by means of tubular insert 21. It is understood that any suitable attaching means may be used.

The catheter body 12 and tip portion 14 may be made of any suitable non-toxic material. In a preferred embodiment, the catheter body 12 and tip portion 14 comprise a single elongated tubular extrusion made of a thermoplastic resin such as polyurethane. One or more layers of a reinforcing braided mesh (not shown) of, for example, stainless steel or dacron, overlie the polyurethane extrusion. The reinforcing mesh is, in turn, coated with a layer of polyurethane or other suitable plastic material.

It is understood that, if desired, the catheter body 12 and tip portion 14 may be separate sections of appropriate tubular material joined together rather than a single extrusion. If separate sections of tubular material joined together, the construction of the catheter body 12 need not be the same as that of the tip portion 14. For example, the catheter body 12 may be reinforced with one or more layers of stainless steel mesh, whereas the tip portion 14 may be reinforced with dacron mesh or simply be unreinforced to increase flexibility.

The first lumen 18 extends the complete length of the catheter body 12 and tip portion 14 and extends through tip ablation electrode 19. First lumen 18 has a diameter of at least 0.03 inch and preferably of at least 0.05 inch.

With reference to FIG. 3, the proximal end of the catheter body 12 includes a splitter fitting 24 wherein the first lumen 18 branches into the interior of side arm 26. The side arm 26 may be constructed in any suitable manner as is well known in the art. As shown, the side arm 26 may comprise a short segment of suitable tubing 27, e.g., polyamide tubing, one end of which is inserted through an opening in the wall of the catheter body 12 and into the first lumen 18 and cemented therein.

The other end of tubing 27 is received by another section of tubing 29 which may, for example, terminate in a luer hub or the like to allow the injection or withdrawal of fluids to or from the first lumen 18. Alternatively, the side arm 26 may be molded integrally with the catheter body 12.

Referring again to FIGS. 1 and 2, the second lumen 20 extends the length of the catheter body 12 and tip portion 14. In the embodiment shown, the second lumen 20 has a diameter of about 0.020 inch and is closed at its distal end. Because of the need for a minimum diameter of at least 0.03 inch and preferably 0.05 inch for the first lumen 18, the second lumen 20 necessarily must be off-axis, i.e., cannot be coaxial with the catheter body.

A tightly wound coil spring 48 is disposed in the portion of the second lumen 20 which extends through the catheter body 12. The proximal and distal ends of the coil spring 48 are fixed, e.g., by glue 49 or the like, to the wall of the catheter body 12, forming the second lumen 20. The coil spring 48 has an outer diameter slightly less than the diameter of the second lumen 20. The inner diameter of the coil spring 48 is about 0.01 inch and extends the entire length of the catheter body 12. The coil spring 48 is tightly wound so it can bend but is non-compressible.

In the embodiment shown in FIG. 1, the coil spring 48 does not extend into the tip portion 14. In the portion of the second lumen 20 which extends into the tip portion 14, there is disposed a flexible, compressible, and preferably lubricous sleeve 38, preferably made of polytetrafluoroethylene.

Figure 4:
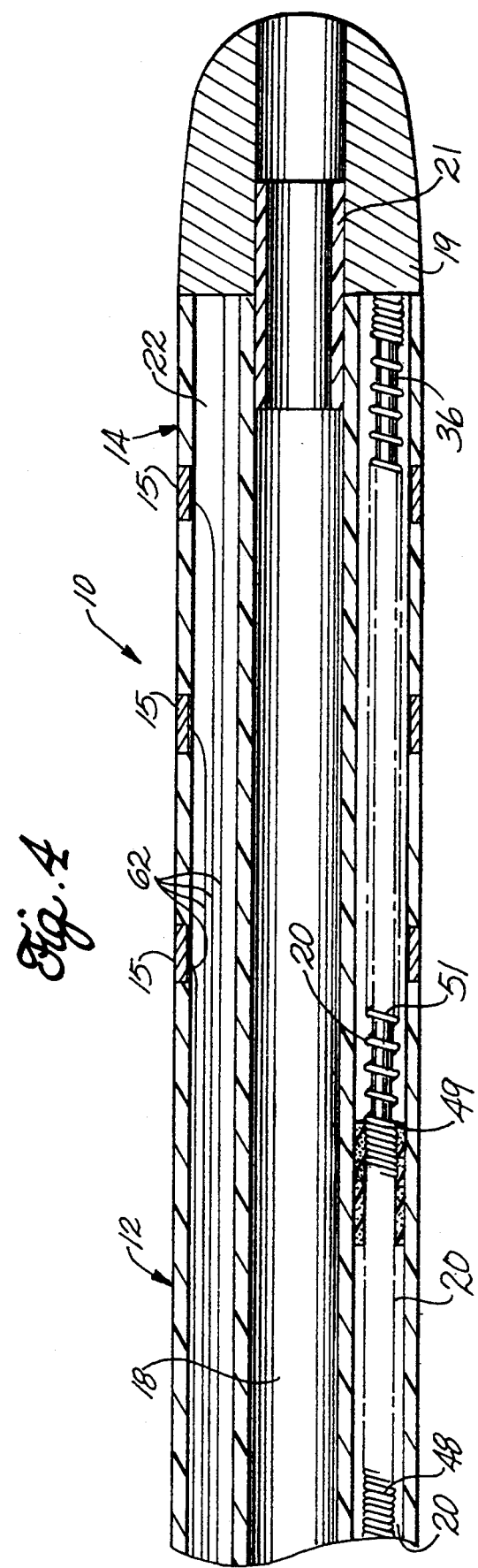
FIG. 4 is a longitudinal offset cross-sectional view of another preferred electrode catheter.

As an alternative to sleeve 38, coil spring 48 may extend completely through the catheter body 12 and tip portion 14 as shown in FIG. 4. In such an embodiment, the portion of the coil spring 48 extending through the second lumen 20 in the catheter body 12 is tightly wound and essentially non-compressible as in FIG. 1. In the tip portion 14, however, the coil spring 51 is loosely wound and therefore flexible and compressible. This can be accomplished, for example, by "stretching" the portion of the coil spring 51 which is to be disposed in the tip portion 14. In this embodiment, the portion of the coil spring 48 in the catheter body 12 must still be fixedly attached, e.g., by glue, to the catheter body 12 at the proximal and distal ends of the catheter body 12.

A puller wire 36, preferably made of stainless steel, having a diameter of about 0.006 inch is disposed within and slidably extends through the coil spring 48 and sleeve 38. Preferably, the puller wire 36 comprises a lubricous coating to prevent the puller wire 36 from sticking to the coil spring 48. The coating is preferably made of a material such as polytetrafluoroethylene which provides excellent non-stick characteristics. Sleeve 38 prevents the puller wire 36 from "cutting through" the wall of the tip portion 14 and also provides lubricity.

The distal end of the puller wire 36 is fixedly attached to the tip electrode 19, e.g., by weld 31 or the like. Alternatively, the puller wire 36 may be fixedly attached to the outer wall of the tip portion 14. A suitable means for attaching the puller wire 36 to the wall of the tip portion 14 of a deflectable catheter is described in U.S. Pat. No. 4,960,134, which is incorporated herein by reference.

Figure 8:
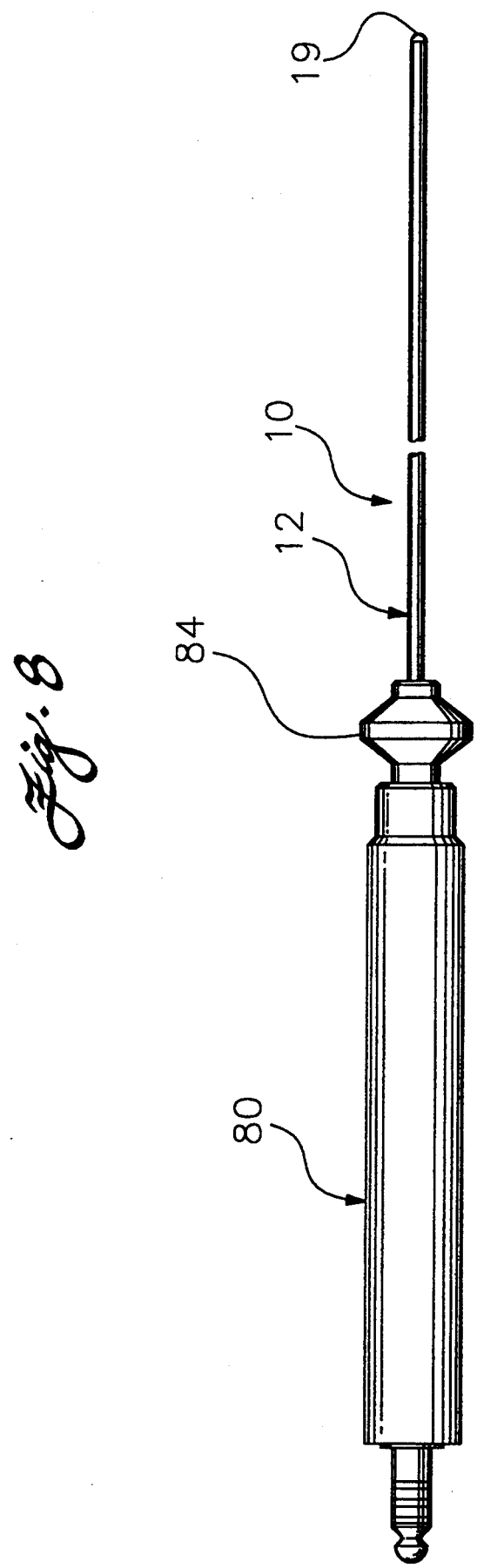
FIG 8 is a side view of the exterior of the catheter to show a control handle of a type suitable for use with the catheter of the invention.

The proximal end of the puller wire 36 is connected to a control handle as is well known in the art. A suitable control handle is disclosed in U.S. Pat. No. 4,960,134, which is incorporated herein by reference. Such a control handle can be used to effectively manipulate the catheter tip portion. FIG. 8 shows the catheter 10 with a control handle 80 at its proximal end. The control handle has an annular flange 84, where it meets the catheter body 12.

The third lumen 22 also extends the length of the catheter body 12 and into the tip portion 14 and is closed at its distal end. The third lumen 22 contains electrode lead wires 62 that are attached at their distal ends to the electrodes carried by the tip portion 14. The lead wires extend to the proximal end of the catheter body 12, through the control handle (not shown) and terminate in a suitable plug as is well known in the art.

The coil spring is rigidly attached by polyurethane glue or the like to the catheter body at its distal and proximal ends. Because the catheter coil spring 48 is noncompressible, tension on the puller wire 36 will not translate into compressive tension on the catheter body 12. The noncompressible coil spring 48 thereby assures that the catheter body 12 does not bend as a result of tension on the puller wire 36 and thereby assumes that rotational control of the catheter 10 is not adversely affected when the puller wire 36 is under tension. By incorporation of the noncompressive coil spring 48, the puller wire 36 can be located off-axis without adverse effect. This, in turn, allows adequate room for the first lumen 18 without the need to increase the overall diameter of the catheter 10.

The presence of an open lumen 18 presents significant advantages. For example, in an RF ablation procedure, the ablation electrode is often "fouled" by the accumulation of coagulum due to overheating. The open lumen, which extends through the ablation electrode 19 enables a cooling fluid, e.g., saline to be passed through the ablation electrode 19, thereby cooling the electrode and preventing overheating. This, in turn, prevents the accumulation of coagulum on the surface of the electrode.

Figure 5:
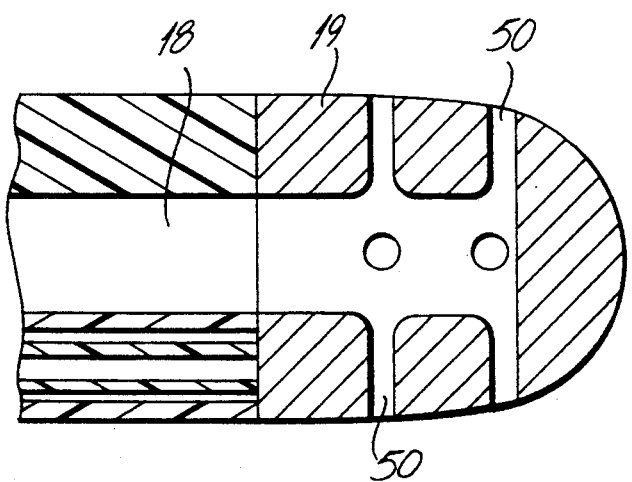
FIG. 5 is a longitudinal cross-sectional view of another ablation tip electrode.

In such an application, if the first lumen 18 is to be used primarily for cooling of an ablation tip electrode 19, it is understood that the portion of the lumen extending through the catheter body 12 can have any desired shape. For example, the lumen can simply extend longitudinally through the tip electrode as shown in FIG. 1. Alternatively, the first lumen 18 may extend into the tip electrode 19 and then separate into one or more radial branches 50 as shown in FIG. 5. Obviously, if the lumen 18 forms branches 50, the number, location and direction of the branches may vary as desired.

Figure 6:
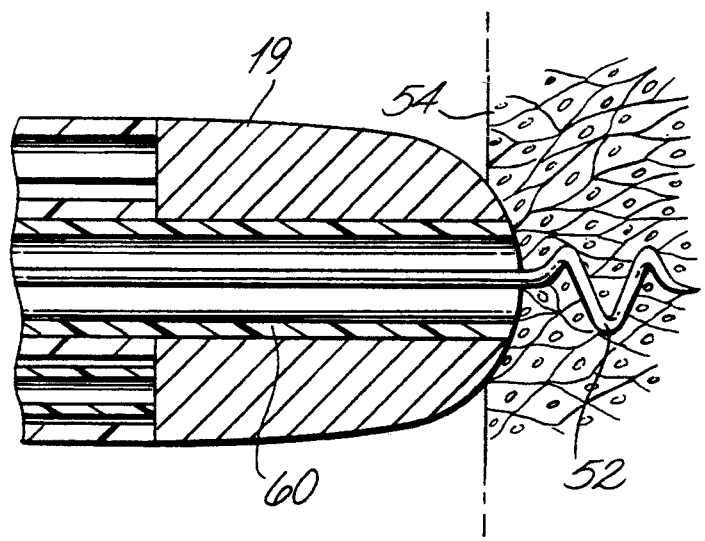
FIG. 6 is a longitudinal cross-sectional view of the distal end of another preferred ablation catheter including an anchor wire.

The first lumen, in addition to facilitating the injection of a fluid through the catheter, may also be used for other purposes. Clearly it could be used for the withdrawal of fluid from the body cavity in which the tip portion 14 of the catheter body 12 lies. As another example, as shown in FIG. 6, an anchor wire 52 may be passed through the first lumen 18 and into the endocardium 54 to anchor the catheter against the endocardium 54. This could be especially useful in an ablation procedure wherein the anchor wire facilitates and assures contact between the ablation electrode and the endocardium. In such an embodiment, it is preferred that the distal end of the anchor wire 52 have a shape which allows it to become solidly anchored in the endocardium 54. A corkscrew shape, as shown in FIG. 6, is presently preferred as such shape allows the anchor wire 52 to be "screwed" into and out of the endocardium without tearing the endocardium tissue.

Figure 7:
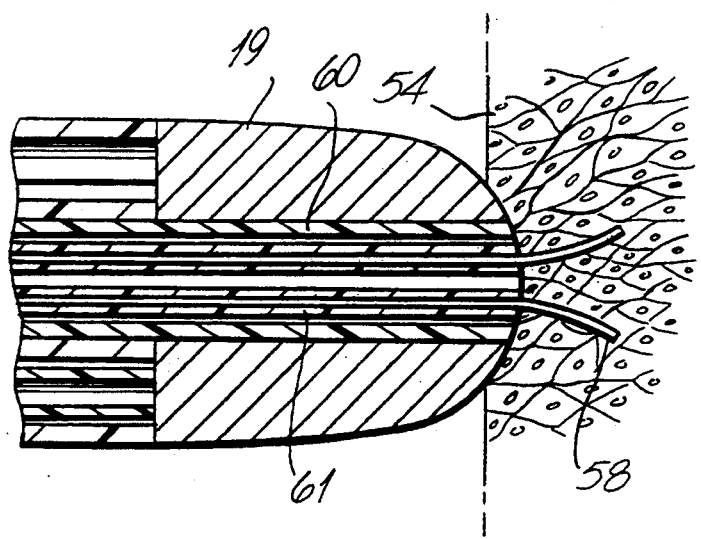
FIG. 7 is a longitudinal cross-sectional view of the distal end of another preferred ablation catheter including an RF antenna.

As another example, as shown in FIG. 7, one or more RF antenna wires 58 may be passed through the first lumen 18 and directly into the endocardium 54 to heat the tissue from within the endocardium 54. In such an embodiment, the RF antenna wires 58 are preferably insulated from the tip electrode 19, if present, and from each other by insulation sleeves 60 and 61. If present, tip electrode 19 may or may not also be used to deliver RF energy, as desired. The RF antennas 58 may be straight or have a preformed shape, as desired.

It is apparent that, if desired, an anchor wire may also be used as an RF antenna for delivering RF energy to the endocardium.

The first lumen could be used for other applications. For example, an optic fiber may be passed through the first lumen for viewing of or delivery of laser radiation to a selected site. A temperature probe may be passed through the first lumen for monitoring temperature. In an ablation procedure, this would enable one, for example, to place a thermistor directly against, or even into, the portion of the endocardium being heated in an RF ablation procedure. This would enable one to monitor the temperature of the tissue being heated and control that temperature by controlling the intensity of the RF current being delivered to the tissue with more precision than current designs offer.

It is understood that the open lumen may perform more than one function, e.g., contain a movable anchor wire and provide a passageway for cooling fluid. It is also understood that more than one open lumen may be provided, e.g., one open lumen for passage of fluids and another for containing an anchor wire, temperature probe, etc.

Thus, while the preceding description has been presented with reference to presently preferred embodiments of the invention, workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable open lumen catheter comprising:
   a flexible, elongated catheter body having proximal and distal ends and a central axis;
   a flexible tip portion at the distal end of the catheter body comprising proximal and distal ends;
   a first lumen extending lengthwise through the catheter body and tip portion, said first lumen being open at the distal end of the tip portion;
   a second lumen extending lengthwise through the catheter body and tip portion, said second lumen being offset from the central axis of the catheter body;
   a bendable, non-compressible coil spring disposed in the second lumen and extending the length of the catheter body, said coil spring having an axis offset from the central axis and being fixedly attached to the catheter body at the proximal and distal ends of the catheter body for stiffening the catheter body against compression;

an elongated puller wire extending through and slidably disposed in the coil spring and extending into the portion of the second lumen in the tip portion and offset from the central axis of the catheter body, said puller wire having a distal end fixedly attached to the distal end of the tip portion and a proximal end fixedly attached to a control handle at the proximal end of the catheter body; and a control handle mounted at the proximal end of the catheter body for moving the puller wire longitudinally relative to the catheter body and coil spring to thereby deflect the tip portion.

2. The steerable catheter of claim 1 wherein the catheter body has an outer diameter of no more than about 0.1 inch.

3. The steerable catheter of claim 2 wherein the first lumen has a diameter of at least about 0.03 inch.

4. The steerable catheter of claim 2 wherein the first lumen has a diameter of at least about 0.05 inch.

5. The steerable catheter of claim 1 further comprising a flexible, compressible, lubricous sleeve in surrounding relation to the portions of the puller wire disposed in the tip portion of the catheter.

6. The steerable catheter of claim 5 wherein the sleeve comprises polytetrafluoroethylene.

7. The steerable catheter of claim 1 wherein the coiled spring extends into the tip portion of the catheter in surrounding relation to the puller wire and wherein the portion of the coiled spring in the tip portion is both bendable and compressible.

8. The steerable catheter of claim 1 further comprising:
    a third lumen extending through the catheter body and tip portion;
    at least one electrode carried by the tip portion; and
    an electrode lead wire attached to each electrode, said electrode lead wires extending through the third lumen to the proximal end of the catheter body.

9. The steerable catheter of claim 1 further comprising a splitter fitting adjacent the proximal end of the catheter body, said splitter fitting comprising a tubular side arm wherein the first lumen branches into the interior of the side arm.

10. The steerable catheter of claim 1 wherein the catheter body and tip portion comprise a unitary extrusion.

11. The steerable catheter of claim 1 wherein the puller wire lies along the axis of the coil spring.

12. The steerable catheter of claim 1 wherein an axis of the first lumen does not coincide with the central axis of the catheter body.

13. A steerable open lumen electrode catheter comprising:
    a flexible, elongated catheter body having proximal and distal ends;
    a flexible tip portion at the distal end of the catheter body comprising proximal and distal ends;
    a first lumen extending lengthwise through the catheter body and tip portion, said first lumen being open at the distal end of the tip portion;
    a second lumen extending lengthwise through the catheter body and tip portion, said second lumen being offset from the axis of the catheter body;
    a coil spring disposed in the second lumen and extending the length of the catheter body, said coil spring being fixedly attached to the catheter body at the proximal and distal ends of the catheter body, and wherein the coil spring is bendable but non-compressible;

an elongated puller wire slidably disposed in and extending through the coil spring and into the second lumen of the tip portion, said puller wire having a distal end fixedly attached to the distal end of the tip portion and a proximal end fixedly attached to a control handle at the proximal end of the catheter body;

a third lumen extending through the catheter body and tip portion;

a control handle mounted at the proximal end of the catheter body for moving the puller wire longitudinally relative to the catheter body and coil spring;

at least one electrode carried by the tip portion; and an electrode lead wire attached to each electrode carried by the tip portion, each of said electrode lead wires extending through the third lumen to the proximal end of the catheter body.

14. The steerable catheter of claim 13 wherein the catheter body has an outer diameter of no more than about 0.1 inch.

15. The steerable catheter of claim 14 wherein the first lumen has a diameter of at least about 0.03 inch.

16. The steerable catheter of claim 14 wherein the first lumen has a diameter of at least about 0.05 inch.

17. The steerable catheter of claim 13 further comprising a splitter fitting adjacent the proximal end of the catheter body, said splitter fitting comprising a tubular side arm and wherein the first lumen branches into the interior of the side arm.

18. A steerable open lumen catheter comprising:
    a flexible, elongated catheter body having proximal and distal ends;
    a flexible tip portion at the distal end of the catheter body comprising proximal and distal ends;
    a first lumen extending lengthwise through the catheter body and tip portion, said first lumen being open at the distal end of the tip portion;
    a second lumen extending lengthwise through the catheter body and tip portion, said second lumen being offset from the axis of the catheter body;
    a bendable, non-compressible coil spring disposed in the second lumen and extending the length of the catheter body, said coil spring being fixedly attached to the catheter body at the proximal and distal ends of the catheter body;
    an elongated puller wire extending through and slidably disposed in the coil spring and extending into the portion of the second lumen in the tip portion, said puller wire having a distal end fixedly attached to the distal end of the tip portion and a proximal end fixedly attached to a control handle at the proximal end of the catheter body;
    a control handle mounted at the proximal end of the catheter body for moving the puller wire longitudinally relative to the catheter body and coil spring to thereby deflect the tip portion.
    a third lumen extending through the catheter body and tip portion;
    at least one electrode carried by the tip portion; and
    an electrode lead wire attached to each electrode, each said electrode lead wire extending through the third lumen to the proximal end of the catheter body.

* * * * *